United States Patent [19]
Huxley et al.

[11] Patent Number: 5,889,020
[45] Date of Patent: Mar. 30, 1999

[54] TREATMENT OF NORMOTENSIVE GLAUCOMA WITH ANGIOTENSIN II ANTAGONISTS

[75] Inventors: Alica Huxley, Binningen; Georg Mathis, Bülach, both of Switzerland

[73] Assignee: CIBA Vision Corporation, Duluth, Ga.

[21] Appl. No.: 682,772

[22] PCT Filed: Jan. 26, 1995

[86] PCT No.: PCT/IB95/00056

§ 371 Date: Jul. 30, 1996

§ 102(e) Date: Jul. 30, 1996

[87] PCT Pub. No.: WO95/21609

PCT Pub. Date: Aug. 17, 1995

[30] Foreign Application Priority Data

Feb. 8, 1994 [EP] European Pat. Off. .............. 94810071

[51] Int. Cl.$^6$ .......................... A61K 31/44; A61K 31/47; A61K 31/41; A61K 31/415
[52] U.S. Cl. .......................... 514/303; 514/311; 514/382; 514/385; 514/913
[58] Field of Search ................................... 514/303, 311, 514/382, 385, 913

[56] References Cited

FOREIGN PATENT DOCUMENTS

0430709A2  11/1990  European Pat. Off. .
WO9210183  6/1992  WIPO .
WO9315732  8/1993  WIPO .

OTHER PUBLICATIONS

Could the Pharmacological Differences Observed Between Antiotensin II Antagonists and Inhibitors of Angiotensin Converting Enzyme be Clinically Beneficial?, Pharmacological & Toxicology 1992, 71, pp. 241–249.

The Ocular Hypotensive Effect of DUP 753, A Non–Peptide Agiotension II Antagonist, S. Wilson, et al., Dept. of Pharmacology, Texas College of Osteopathic Medicine, Fort Worth, TX 76107 (Abstract).

Angiotensin II Receptors Labelled with 125I[Sar, Ile8]–All in Albino Rabbit Ocular Tissues, P., Mallorga, et al., Current Eye Research, IRL Press, vol. 8, 1989, p. 841.

Angiotensin Receptor Subtypes in the Albino Rabbit Eye, Mallorga, P., et al., Society for Neuroscience Abstracts, vol. 17, p. 810,1991.

Nonpeptide Angiotensin II Receptor Antagonists: A New Concept for Pharmacologic Control of the Renin System, American Journal of Hypertension, vol. 4, No. 4, Part 2, Apr., 1991.

Are Large Optic Nerve Heads Susceptible to Glaucomatous Damage at Normal Intraocular Pressure?, Burk, Reinhard O.W., et al., Graefe's Archive Ophthalmology, vol. 230, No. 6, 1992.

Optic Nerve Compression By CartotidArteries in Low–Tension Glaucoma,, Gutman, Isaac, et al., Graefe's Archive for Clinical and Experimental Ophthalmology, Dec., 1993.

Chemical Abstracts 119:174228 (1993), Cash et al.

*Primary Examiner*—Zohreh Fay
*Attorney, Agent, or Firm*—Michael U. Lee; R. Scott Meece

[57] ABSTRACT

The present invention relates to the use of angiotensin antagonist or a pharmaceutically acceptable salt thereof for the treatment of normal tension glaucoma, wherein said angiotensin antagonist and salt thereof have pronunced selectivity for the AT1 receptor.

4 Claims, No Drawings

TREATMENT OF NORMOTENSIVE GLAUCOMA WITH ANGIOTENSIN II ANTAGONISTS

This application is a 371 of PCT/IB95/00056 filed on Jan. 26, 1995.

The present invention describes the use of an angiotensin II antagonist or of a pharmaceutically acceptable salt thereof in the preparation of a pharmaceutical composition for the treatment of normal tension glaucoma and neurodegenerative processes.

The term glaucoma includes symptoms of the eye which are especially to be attributed to increased intraocular pressure. Frequently, an obstruction to drainage of the aqueous humour leads to an increase in the intraocular pressure. Chronically raised intraocular pressure has a harmful effect on the optic nerve and the retina, which can terminally lead to blindness. Accordingly, for the treatment of glaucoma, active ingredients are used which are able to reduce significantly the intraocular pressure. Renin inhibitors have been mentioned, for example, as suitable agents for lowering the intraocular pressure (cf. Watkins, U.S. Pat. No. 4,906,613). Increased intraocular pressure can also be treated with certain β-adrenoceptor blockers.

More recently, the phenomenon of so-called normal tension glaucoma ("low tension" or "normal tension glaucoma" is used synonymously) has now been clinically established in ophthalmology [J. Flammer, Fortschr. Ophthalmol. 87, 187(1990)]. Normal tension glaucoma is characterized by an intraocular pressure which is in the normal range, i.e. is not increased, but in which the optic disc (papilla nervi optici) is pathologically excavated and the field of vision is impaired. The pathogenetic factors are especially circulatory problems in the ocular blood vessels caused by atherosclerosis, hypotension, orthostasis, functional vasospasms and neurodegenerative factors.

Accordingly, a therapy for the treatment of normal tension glaucoma therefore starts with the possible factors involved mentioned above. Actually, this means that active ingredients which are able to guarantee or to improve the circulation in the ocular blood vessels are suitable agents for the treatment of normal tension glaucoma and of neurodegenerative factors.

It has now surprisingly been found that angiotensin II antagonists, preferably those having pronounced selectivity for the $AT_1$ receptor (also called A II blockers in the following), in general and already preclinically established A II blockers such as, for example, valsartan or losartan in particular, extremely improve the circulation in the eye generally and the ocular blood microcirculation in the choroidal and retinal ocular tissue especially. A II blockers are also suitable for treating narrowed visual field or disorders on account of neurological pathogenesis. Such A II blockers are therefore suitable agents for treating the disease of normal tension glaucoma and neurodegenerative processes.

Such A II blockers typically have a preference of $\geq 99\%$ and preferably of $\geq 99.99\%$ for the $AT_1$ receptor in comparison to the $AT_2$ receptor.

In addition to the A II blockers mentioned, there are also mixed or dual angiotensin II antagonists. Dual angiotensin II antagonists have preferences of the same order of magnitude for the $AT_1$ and the $AT_2$ receptor, the relative extent varying greatly. A dual A II blocker having a preference for the $AT_1$ receptor of $\geq 50\%$, preferably $\geq 90\%$ and especially preferably of $\geq 95\%$, is also suitable for treating the disease of normal tension glaucoma.

$AT_2$ receptor antagonists having a preference of $>99\%$ for the $AT_2$ receptor do not have the abovementioned effect on the microcirculation in the eye and are therefore unsuitable for use in the treatment of normal tension glaucoma In the following, if angiotensin II antagonists are being discussed, both A II blockers having the mentioned selectivity for the $AT_1$ receptor, and dual angiotensin II antagonists having the mentioned preference for the $AT_1$ receptor are meant.

The present invention therefore relates to the use of an angiotensin II antagonist or of a pharmaceutically acceptable salt thereof in the preparation of a pharmaceutical composition for the treatment of normal tension glaucoma and neurodegenerative processes.

Examples of angiotensin II antagonists include, but are not restricted to the classes of compound mentioned below and preferred individual compounds selected therefrom which have been disclosed under the patent number given in each case.

EP 253 310 describes A II blockers having the following general formula (I)

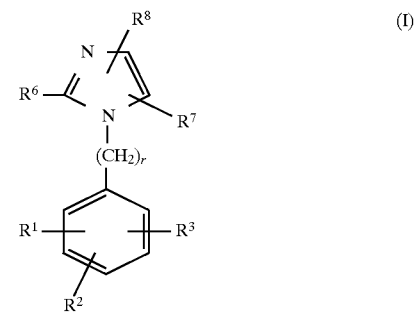

where the variables are as defined in the publication mentioned.

A preferred compound from EP 253 310 is DuP 753 (losartan), having the formula (Ia).

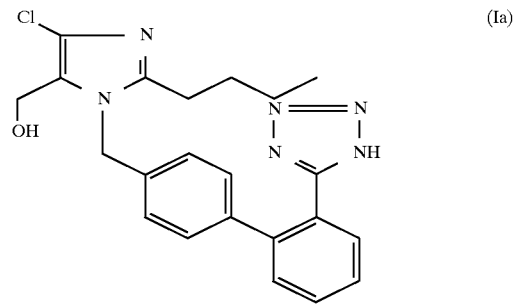

EP 324 377 discloses imidazole derivates as angiotensin II antagonists having the general formula (II)

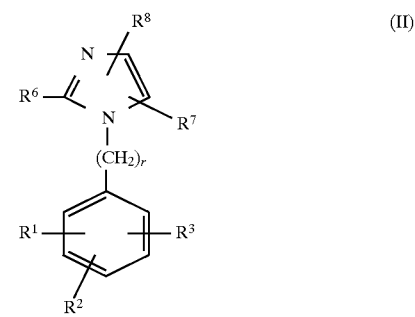

where the variables are as defined in the publication mentioned.

A preferred compound from EP 324 377 is DuP 532 having the formula (IIa).

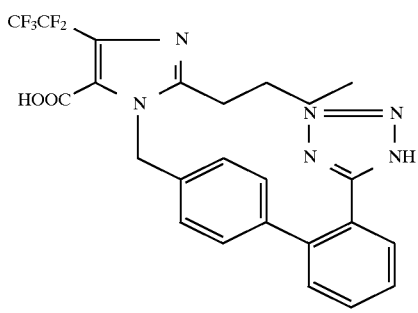

EP 392 317 describes benzimidazoles of the formula (III) as A II blockers

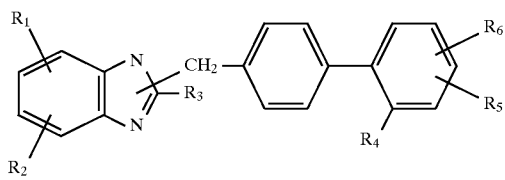

where the variables are as defined in the publication mentioned.

A preferred compound from EP 392 317 is BIBS 39, having the formula (IIIa).

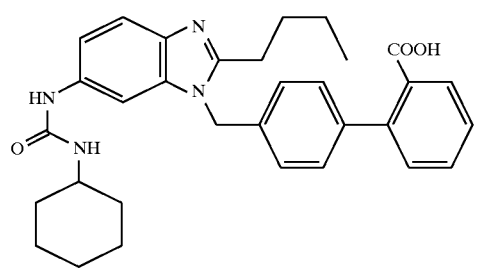

EP 400 974 describes imidazole derivates of the formula (IV) as angiotensin II antagonists

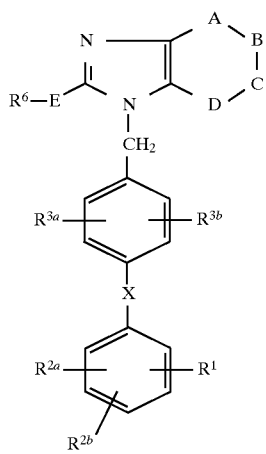

where the variables are as defined in the publication mentioned.

A preferred compound from EP 400 974 is L-158,809, having the formula (IVa).

EP 403 159 describes angiotensin II antagonists of the formula (V)

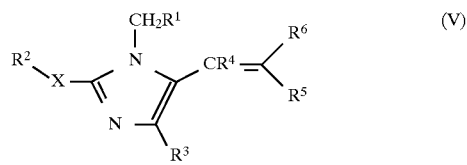

where the variables are defined as in the publication mentioned.

A preferred compound from EP 403 159 is SKF 108 566 having the formula (Va).

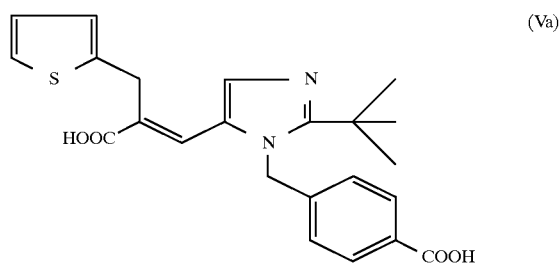

EP 412 848 describes quinoline derivatives of the formula (VI) as A II blockers

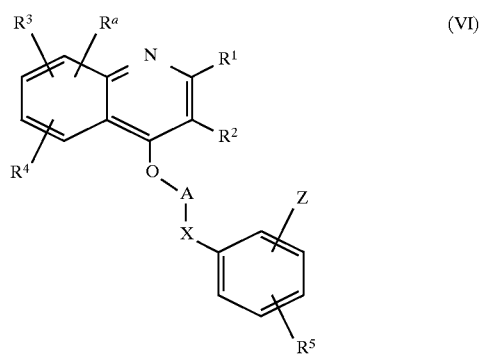

where the variables are as defined in the publication mentioned.

Preferred compounds from EP 412 848 are ICI-D-8731 having the formula (VIa) and ICI-D-6888 having the formula (VIb).

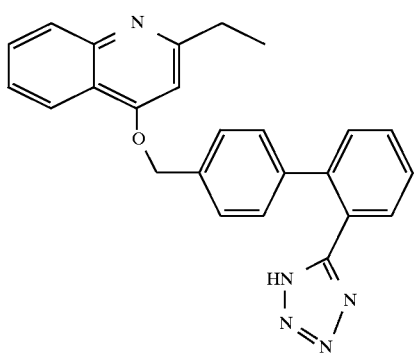
(VIa)

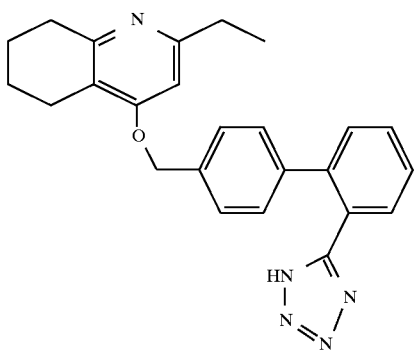
(VIb)

Other imidazole derivates of the formula (VII) are described as A II blockers in EP 426 021

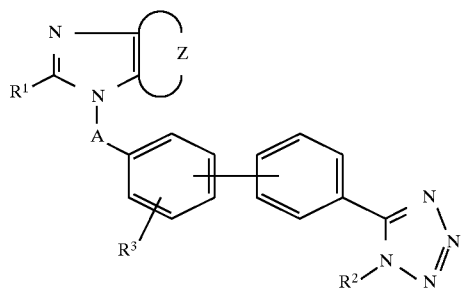
(VII)

where the variables are as defined in the publication mentioned.

A preferred compound from EP 426 021 is FR 130 739 having the formula (VIIa).

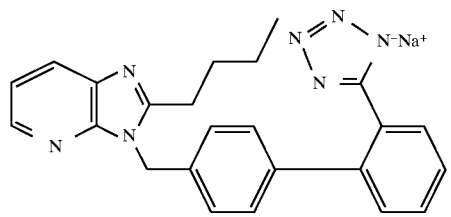
(VIIa)

EP 434 249 describes benzofuran derivatives of the formula (VIII) as A II blockers

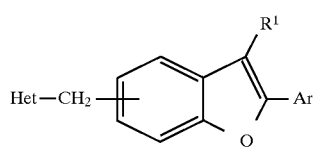
(VIII)

where the variables are as defined in the publication mentioned.

A preferred compound from EP 434 249 is GR 117 289 having the formula (VIIIa).

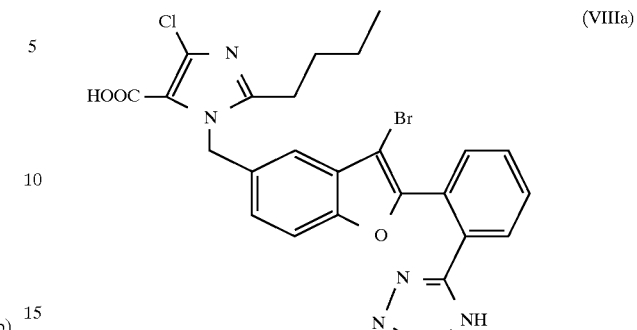
(VIIIa)

EP 443 983 describes angiotensin II antagonists of the formula (IX)

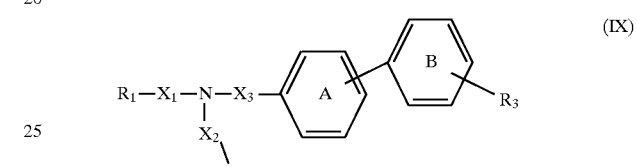
(IX)

where the variables are as defined in the publication mentioned.

A preferred compound from EP 443 983 is CGP 48933 (valsartan) having the formula (IXa).

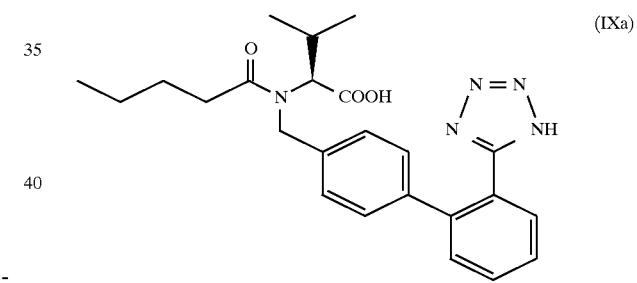
(IXa)

The PCI Application WO 91/14679 describes A II blockers of the formula X)

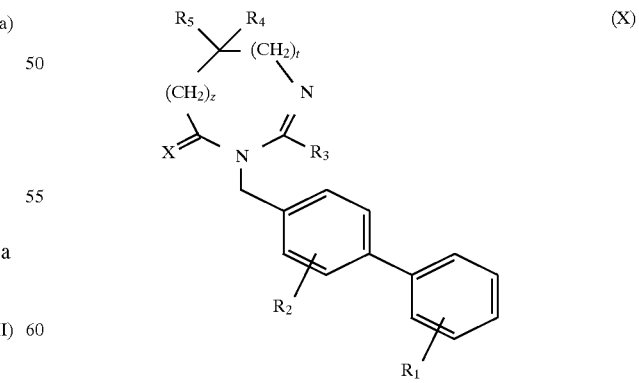
(X)

where the variables are as defined in the publication mentioned.

A preferred compound from WO 91/14679 is SR 47 436, having the formula (Xa).

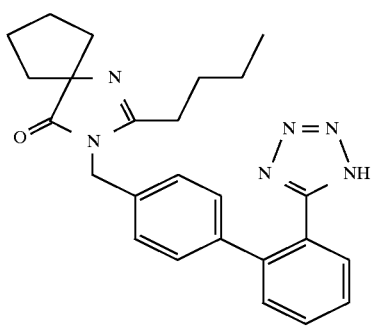

(Xa)

EP 459 136 describes benzimidazoles of the formula (XI) as angiotensin II antagonists

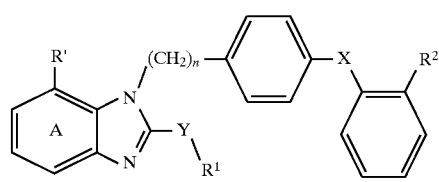

(XI)

where the variables are as defined in the publication mentioned.

A preferred compound of EP 459 136 is TCV 116 having the formula (XIa).

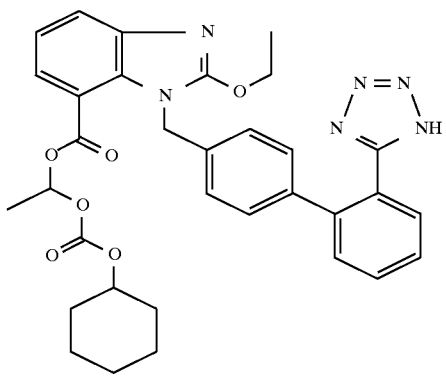

(XIa)

The PCT Application WO 91/17148 describes triazole derivates of the formula (XII) as angiotensin II antagonists

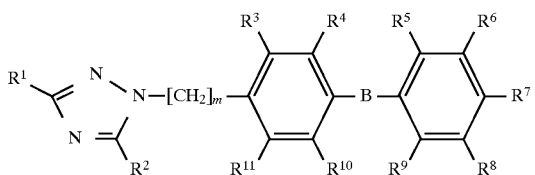

(XII)

where the variables are as defined in the publication mentioned.

A preferred compound from WO 91/17148 is SC 50 560 having the formula (XIIa).

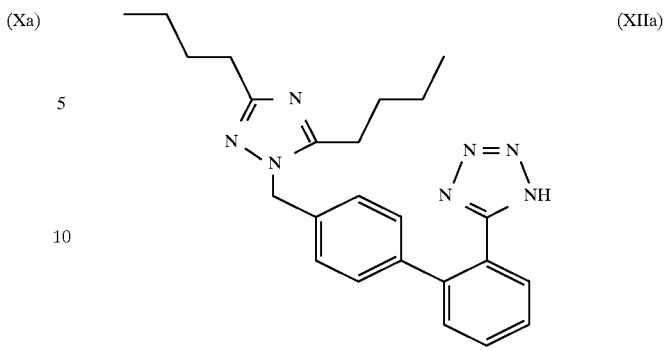

(XIIa)

EP 475 206 describes angiotensin II antagonists of the general formula (XIII)

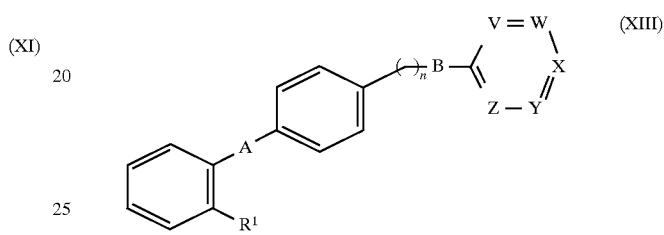

(XIII)

where the variables are as defined in the publication mentioned.

A preferred compound from EP 475 206 is A-81988, having the formula (XIIIa).

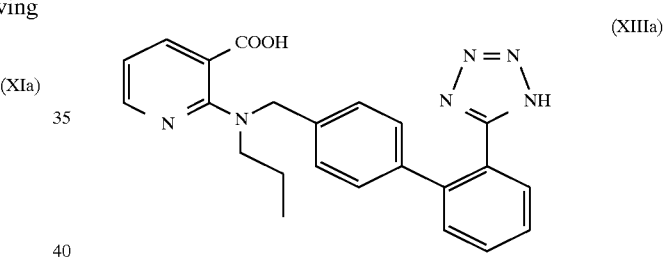

(XIIIa)

DE 4 031 635 describes benzimidazoles of the formula (XIV) as angiotensin II antagonists

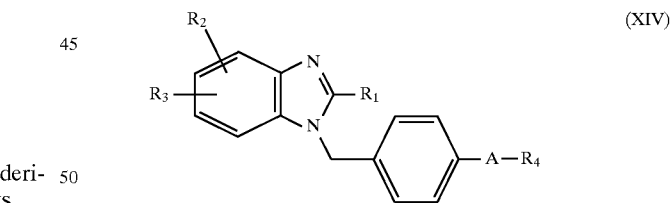

(XIV)

where the variables are as defined in the publication mentioned.

A preferred compound from DE 4 031 635 is BIBS-222, having the formula (XIVa).

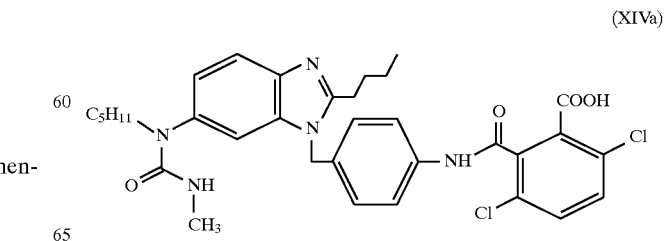

(XIVa)

EP 514 198 describes compounds of the formula (XV), which antagonize the effect of angiotensin II

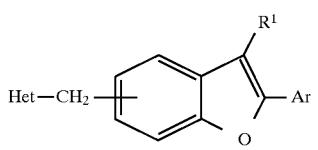

where the variables are as defined in the publication mentioned.

A preferred compound from EP 514 198 is GR-138 950, having the formula (XVa).

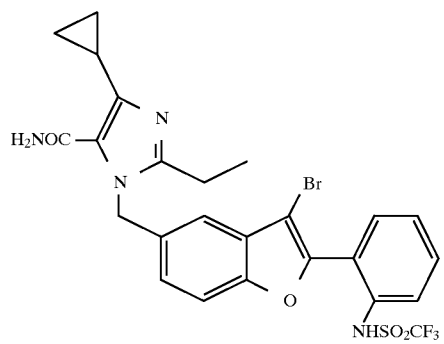

The invention further relates to the use of one of the preferred angiotensin II antagonists (Ia) to (XVa) in the preparation of a pharmaceutical composition for the treatment of normal tension glaucoma.

The angiotensin II antagonists claimed generically (including preferably generically) and specifically in the abovementioned patent applications are hereby incorporated by reference as compounds to be used according to the invention.

All the abovementioned A II blockers are suitable for the medicinal use disclosed Highly effective A II blockers which can antagonize the action of angiotensin II to $\geq 50\%$ at a concentration of $\leq 1$ $\mu$M are particularly preferred. A II blockers which can antagonize the action of angiotensin II to $\geq 50\%$ at a concentration of $\leq 10$ nM are therefore furthermore especially preferred.

Methods for the determination of the $AT_1$ binding on the one hand, and pharmacological tests for the quantitative determination of the angiotensin II effect on the other hand are described, for example, in: J. V. Duncia et al., Drugs of the Future 17, 326(1992); or V. J. Dzau et al., The Heart and Cardiovascular System, pages 1631–1662 (1986), Raven Press, New York, H. A. Fozzard, E. Haber, R. B. Jennings, A. M. Katz, H. E. Morgan (Editors).

The angiotensin II antagonists can be present as salts, in particular pharmaceutically acceptable salts. The angiotensin II antagonists, which have e.g. at least one basic centre, can form acid addition salts. These are formed, for example, with strong inorganic acids, such as mineral acids, e.g. sulfuric acid, a phosphoric acid or a hydrohalic acid, with strong organic carboxylic acids, such as $C_1$–$C_4$alkanecarboxylic acids which are unsubstituted or substituted e.g. by halogen, e.g. acetic acid, such as saturated or unsaturated dicarboxylic acids, e.g. oxalic, malonic, succinic, maleic, fumaric, phthalic or terephthalic acid, such as hydroxycarboxylic acids, e.g. ascorbic, glycolic, lactic, malic, tartaric or citric acid, such as amino acids, e.g. aspartic or glutamic acid, or such as benzoic acid, or with organic sulfonic acids, such as $C_1$–$C_4$alkane- or arylsulfonic acids which are unsubstituted or substituted e.g. by halogen, e.g. methane- or p-toluenesulfonic acid. Corresponding acid addition salts can also be formed which may additionally have a basic centre.

Angiotensin II antagonists which carry at least one acidic group can further form salts with bases. Suitable salts with bases are, for example, metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkylamine, e.g. ethyl-, tert-butyl-, diethyl-, diisopropyl-, triethyl-, tributyl- or dimethylpropylamine, or a mono-, di- or trihydroxy-lower alkylamine, e.g. mono-, di- or triethanolamine. Corresponding internal salts can furthermore be formed.

As a result of the close relationship between an angiotensin II antagonist in free form and in the form of a salt, hereinbefore and hereinafter a free compound is correspondingly and expediently to be understood, where appropriate, as also meaning a corresponding salt, or a salt is also to be understood as meaning a corresponding free compound.

The present application further relates to a pharmaceutical composition for the treatment of normal tension glaucoma, comprising a therapeutically effective amount of an angiotensin II antagonist or of a pharmaceutically acceptable salt thereof, and a pharmaceutically acceptable formulating agent which is suitable for topical application, in particular ophthalmic and systemic administration.

The present invention furthermore relates to an ophthalmic composition for the treatment of normal tension glaucoma, comprising a therapeutically effective amount of an angiotensin II antagonist or a pharmaceutically acceptable salt thereof.

The present invention furthermore relates to an ophthalmic composition for the treatment of normal tension glaucoma, comprising a therapeutically effective amount of (S)-N-(1-carboxy-2-methylprop-1-yl)-N-pentanoyl-N-[2'-(1H-tetrazol-5-yl)-biphenyl4-ylmethyl ]amine or of a pharmaceutically acceptable salt thereof.

An appropriate ophthalmic composition is applied to the eye topically, in particular in the form of a solution, an ointment, a gel or a solid insert. Compositions of this type contain the active compound, for example, in a range from about 0.000001 to about 5.0% by weight, preferably from about 0.001 to about 1.0% by weight, or in the range from about 0.01 to about 0.5% by weight. The dose of the active compound can depend on various factors, such as administration procedure, need, age and/or individual condition.

Customary pharmaceutically acceptable adjuncts and additives, for example of the type mentioned below, known to the person skilled in the art are used for an appropriate ophthalmic composition, in particular carriers, solubilizers, tonicity-increasing agents, buffer substances, preservatives, thickeners, complexing agents and other adjuncts. Examples of additives and adjuncts of this type are found in U.S. Pat. No. 5,134,124 and U.S. Pat. No. 4,906,613. The manufacture of such compositions is carried out in a manner known per se, i.e. the active ingredient is mixed with the appropriate adjuncts and/or additives to give corresponding ophthalmic compositions. Preferably, the active ingredient is administered in the form of eye drops, the active ingredient being dissolved, for example, in a carrier by means of a solubilizer. If desired, adjustment to the desired pH and/or buffering is carried out and if desired a tonicity-increasing agent is added. If desired, preservatives and/or other adjuncts complete an ophthalmic composition.

In order to prepare suitable formulations, the active ingredient of an angiotensin II antagonist is mixed with a carrier suitable for topical or general administration. Suitable carriers are especially water, mixtures of water and water-miscible solvents such as lower alkanols, vegetable oils or mineral oils comprising 0.5–5% by weight of hydroxyethylcellulose, ethyl oleate, carboxymethylcellulose, polyvinylpyrrolidone and other non-toxic water-soluble polymers intended for ophthalmic use such as e.g. cellulose derivatives such as methylcellulose, alkali metal salts of carboxymethylcellulose, hydroxymethylcellulose, hydroxyethylcellulose and hydroxypropylcellulose, acrylates or methacrylates such as salts of polyacrylic acid or ethyl acrylate, polyacrylamides, natural products such as gelatin, alginates, pectins, tragacanth, karaya gum, xanthan gum, carrageenan, agar and acacia, starch derivatives such as starch acetate and hydroxypropyl starch, and also other synthetic products such as polyvinyl alcohol, polyvinylpyrrolidone, polyvinyl methyl ether, polyethylene oxide, preferably crosslinked polyacrylic acid such as neutral carbopol or mixtures of these polymers. The concentration of the carrier is, for example, 1- to 100,000-times the active ingredient concentration.

Solvents used for the angiotensin II antagonists used are, for example, fatty acid glycerol polyglycol esters, fatty acid polyglycol esters, polyethylene glycols, glycerol ethers or mixtures of these compounds. A specific example of a particularly preferred solubilizer is a reaction product of castor oil and ethylene oxide, for example the commercial product Cremophor EL®. Reaction products of castor oil and ethylene oxide have proven particularly good solubilizers having an excellent ophthalmic tolerability. The concentration used primarily depends on the concentration of the active ingredient. At least sufficient is to be added that the active ingredient is brought into solution. As an example, the concentration of the solubilizer is 1- to 1000-times the active ingredient concentration.

Examples of buffer substances are acetate, ascorbate, borate, bicarbonate/carbonate, citrate, gluconate, lactate, phosphate, propionate and tris buffers. The amount of buffer substance is added, for example, which is necessary to guarantee and to maintain a physiologically tolerable pH range.

Tonicity-enhancing agents are, for example, ionic compounds, such as alkali metal or alkaline earth metal halides such as e.g. $CaCl_2$, KBr, KCl, LiCl, NaI, NaBr or NaCl, or boric acid. Non-ionic tonicity-enhancing agents are e.g. urea, glycerol, sorbitol, mannitol propylene glycol or dextrose. Sufficient tonicity-enhancing agent is added, for example, that the ready-to-use ophthalmic composition has an osmolality of about 50 to 400 mOsmol.

Examples of preservatives are quaternary ammonium salts such as cetrimide, benzalkonium chloride or benzoxonium chloride, alkylmercury salts of thiosalicylic acid such as e.g. thiomersal, phenylmercury nitrate, phenylmercury acetate or phenylmercury borate, parabens such as e.g. methylparaben or propylparaben, alcohols such as e.g. chlorobutanol, benzyl alcohol or phenylethanol, guanidine derivatives such as e.g. chlorhexidine or polyhexamethylenebiguanide, or sorbic acid. If desired, the amount of preservative which is necessary to guarantee sterility is added to the ophthalmic composition.

The ophthalmic compositions can further contain non-toxic adjuncts such as, for example, emulsifiers, wetting agents or fillers such as e.g. the polyethylene glycols designated 200, 300, 400 and 600, or Carbowax designated 1000, 1500, 4000, 6000 and 10,000. Other adjuncts used if desired are mentioned below, but should not restrict the range of the possible adjuncts in any manner. In particular, they are complexing agents such as disodium EDTA or EDTA, antioxidants such as ascorbic acid, acetylcysteine, cysteine, sodium bisulfite, butylhydroxyanisole, butylhydroxytoluene or α-tocopherol acetate, stabilizers such as β-cylodextrin, hydroxypropyl-β-cylodextrin, thiourea, thiosorbitol, sodium dioctylsulfosuccinate or monothioglycerol, or other auxiliaries such as e.g. lauric acid sorbitol ester, triethanolamine oleate or palmitic acid esters. The amount and the nature of the adjunct added depends on the specific requirements, and as a rule is in the range from about 0.0001 to about 90% by weight.

The present application further relates to an ophthalmic composition for the treatment of normal tension glaucoma, comprising a therapeutically effective amount of an angiotensin II antagonist or of a pharmaceutically acceptable salt thereof and another, therapeutically effective, pharmaceutical. This can be, for example, an antibiotic, β-blocker, calcium antagonist, anaesthetic, an antiinflammatory, a composition suitable for the treatment of intraocular pressure or another pharmacon.

The invention likewise relates to the use of an angiotensin II antagonist, or of a pharmaceutically acceptable salt thereof, in the preparation of a systemically administrable pharmaceutical composition for the treatment of normal tension glaucoma.

These pharmaceutical compositions are those for enteral administration, such as oral administration, and also rectal or parenteral administration to warm-blooded animals, the pharmacological active ingredient being contained on its own or together with customary pharmaceutical adjuncts. The pharmaceutical compositions contain e.g. about 0.1% to 100%, preferably from about 1% to about 60%, of the active ingredient. Pharmaceutical compositions for enteral or parenteral and also for ocular administration are e.g. those in unit dose form, such as sugar-coated tablets, tablets, capsules or suppositories, and also ampoules. These are prepared in a manner known per se, e.g. by means of conventional mixing, granulating, sugar coating, dissolving or lyophilizing processes. Pharmaceutical compositions for oral administration can thus be obtained by combining the active ingredient with solid carriers, if desired granulating a mixture obtained, and processing the mixture or granules, if desired or necessary after addition of suitable adjuncts, to give tablets or sugar-coated tablet cores.

Suitable carriers are, in particular, fillers, such as sugars, e.g. lactose, sucrose, mannitol or sorbitol, cellulose compositions and/or calcium phosphates, e.g. tricalcium phosphate or calcium hydrogen phosphate, and also binders, such as starch pastes, using e.g. maize, wheat, rice or potato starch, gelatin, tragacanth gum, methylcellulose and/or polyvinylpyrrolidone, and, if desired, disintegrants, such as the abovementioned starches, and also carboxymethyl starches, crosslinked polyvinylpyrrolidone, agar or alginic acid or a salt thereof, such as sodium alginate. Adjuncts are primarily flow regulators and lubricants, e.g. silicic acid, talc, stearic acid or salts thereof, such as magnesium stearate or calcium stearate, and/or polyethylene glycol. Sugar-coated tablet cores are provided with suitable coatings which are, if desired, enteric-resistant, concentrated sugar solutions which if desired contain gum arabic, talc, polyvinylpyrrolidone, polyethylene glycol and/or titanium dioxide, lacquer solutions in suitable organic solvents or solvent mixtures or, for the composition of enteric-resistant coatings, solutions of suitable cellulose compositions, such as acetylcellulose phthalate or hydroxypropylmethylcellulose phthalate, being used inter alia. Colourants or pigments, e.g. for the identification or for the characterization of various doses of active ingredient, are added to the tablets or the sugar-coated tablet coatings.

Other orally administrable pharmaceutical compositions are hard capsules made of gelatin and soft, closed capsules made of gelatin and a softener, such as glycerol or sorbitol. The hard capsules can contain the active ingredient in the form of granules, e.g. in a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, liquid paraffin or liquid polyethylene glycols, it also being possible to add stabilizers.

Suitable rectally administrable pharmaceutical compositions are e.g. suppositories, which consist of a combination of the active compound with a suppository base. Suitable suppository bases are e.g. natural or synthetic triglycerides, paraffin hydrocarbons, polyethylene glycols and higher alkanols. Gelatin rectal capsules which contain a combination of the active compound with a base substance can also be used. Possible base substances are e.g. liquid triglycerides, polyethylene glycols and paraffin hydrocarbons.

Aqueous solutions of an active ingredient in water-soluble form, e.g. of a water-soluble salt, also suspensions of the active ingredient, such as appropriate oily injection suspensions, are primarily suitable for parenteral administration, suitable lipophilic solvents or vehicles, such as fatty oils, e.g. sesame oil, or synthetic fatty acid esters, e.g. ethyl oleate or triglycerides, being used, or aqueous injection suspensions which contain viscosity-increasing substances, e.g. sodium carboxymethylcellulose, sorbitol and/or dextran, and if desired also stabilizers.

The dose of the active ingredient can depend on various factors, such as manner of administration, warm-blooded animal species, age and/or individual condition.

Two methods are especially suitable for the measurement of the improvement of the blood circulation in the eye. One is the so-called myograph system for isolated extraocular arteries and the second is the perfusion system in the intact isolated eye, for example a pig's eye.

For the myographic determinations, a short segment (7–8 mm) of the ciliary arteries of fresh eyes, e.g. pig's eyes, is dissected and cut into small rings of thickness 2 mm under a microscope (cf. for this K. Yao et al. Invest. Ophthalmaol. Vis. Sci. 32, 1791–1798(1991) and M. J. Mulvany, W. Halpern Circ. res. 41, 19–26(1977)). During the preparation, the tissue is immersed in modified Krebs-Ringer bicarbonate solution. These rings (diameter about 200–400 $\mu$m) are installed in the myograph system without delay. Such a tissue ring is stretched using two tungsten wires (diameters 30 and 80 $\mu$m), the wires being passed through the lumen. One wire is connected to the power transmission, the other to a micromanipulator for adjustment of muscle length. The tissue ring is immersed in a control solution during the experiment (37°; 95% $O_2$; 5% $CO_2$; pH=7.4) and equilibrated for 45 minutes before testing.

The tissue ring is stretched stepwise and at the same time 100 mM KCl is added in each case. The optimum passive tension is then defined as the tension at which the contraction with 100 mM KCl is greatest. For ciliary arteries, an averaged value for the tension of 977 mg±60 mg is found. The active residual tone of this tissue is defmed as the difference between the optimum passive tension and the tension after a maximum relaxation with $10^{-6}$ molar bradykinin. The corresponding tension is 174 mg±38 mg. In all subsequent experiments, the abovementioned tissue rings are slowly stretched at 100 mg intervals until the optimum is reached.

Before the actual experiment, the endothelial function of such a tissue ring is checked for intactness. The tissue rings are challenged to contract by using $3 . 10^{-7}$ molar serotonin solution and in the experimental procedure described above. Thereafter it is checked whether a complete relaxation of the contracted tissue ring occurs with $3 . 10^{-7}$ molar bradykinin solution. If this condition is fulfilled, the tissue is held to be intact.

For the perfusion method on the isolated pig's eye, the fatty tissue which surrounds the extraocular muscles is carefully removed. During this preparation, the ocular globe is surrounded with modified Krebs-Ringer bicarbonate solution at 4° C. The ocular globe is then cannulated under the microscope using a polyethylene cannula (600 $\mu$m diameter), namely via the common ophthalmic artery.

Following this preparation, the ocular globe is connected via the polyethylene cannula to a Langendorff perfusion system, and in this way supplied at the latest 1 hour after the start of preparation with a filtered and oxygenated Krebs solution which contains 0.5% albumin.

The catheterization of the common ophthalmic artery guarantees the complete perfusion both of the choroidal and of the retinal tissue and of the small extraocular muscular arteries. The perfused ocular globe is immersed in a thermostated (37° C.) control bath with a glass jacket with the cornea pointed downwards. The overflow rate (ml/min) in the bath corresponds to the ophthalmic flow. Before testing a composition, the ocular globe is equilibrated for 20 minutes. In a control experiment, it is shown that the ophthalmic flow in the experimental procedure selected remains constant for about 120 minutes after the start of the perfusion. All tests are therefore carried out within this time frame.

The invention likewise relates to a method of treating normal tension glaucoma, which method comprises administering a therapeutically effective amount of an angiotensin II antagonist or of a pharmaceutically acceptable salt thereof to a patient who needs such a treatment.

The following examples illustrate the invention described above; however, they should not restrict this in its scope in any way. Temperatures are given in degrees Celsius.

FORMULATION EXAMPLES 1, 2 and 3

A solution, comprising 20 mg of active compound, e.g. valsartan=(S-N-(1-carboxy-2-methylprop- 1-yl)-N-pentanoyl-N-[2'-(1H-tetrazol-5-yl)biphenyl-4-ylmethyl]amine, can be prepared composed as follows:

| Composition: | |
|---|---|
| 1) | |
| Active ingredient | 20.00 mg |
| 1N NaOH | 86.00 mg |
| Benzalkonium chloride | 0.10 mg |
| Disodium ethylenediaminetetraacetate | 0.50 mg |
| Sorbitol | 10.00 mg |
| $Na_2HPO_4.2\ H_2O$ | 9.91 mg |
| $K_2HPO_4$ | 0.44 mg |
| Water (purity: for inj.) to | 1.00 ml |
| 2) | |
| Active ingredient | 20.00 mg |
| 1N NaOH | 86.00 mg |
| Macrogol 400 | 20.00 mg |
| Benzalkonium chloride | 0.10 mg |
| Disodium ethylenediaminetetracetate | 0.50 mg |
| Sorbitol | 6.00 mg |
| $Na_2HPO_4.2\ H_2O$ | 9.73 mg |
| $K_2HPO_4$ | 0.43 mg |
| Water (purity: for inj.) to | 1.00 ml |

-continued

Composition:

3)

| | |
|---|---|
| Active ingredient | 20.00 mg |
| 1N NaOH | 86.00 mg |
| Polyoxyl 35 castor oil | 4.00 mg |
| Benzalkonium chloride | 0.10 mg |
| Disodium ethylenediaminetetraacetate | 0.50 mg |
| Sorbitol | 6.00 mg |
| $Na_2HPO_4 \cdot 2\, H_2O$ | 9.91 mg |
| $K_2HPO_4$ | 0.44 mg |
| Water (purity: for inj.) to | 1.00 ml |

For this purpose, the ingredients are added to water and dissolved.

Another A II antagonist or a pharmaceutically acceptable salt thereof can be processed in an analogous manner, for example as described in the above examples.

EXAMPLE 4

Determination of the ciliary artery contraction using the myograph method

After it was verified as described above that the endothelial functions of a tissue ring of a ciliary artery are intact, the tissue ring preparation is incubated (contracted) with $10^{-7}M$ angiotensin II, and then relaxed with various doses of the angiotensin II antagonist valsartan. The results are presented below:

| Dose of valsartan | Relative contraction in comparison to 100 mM KCl (in %) |
|---|---|
| 0 (control) | 27.9 ± 8.7 (pure angiotensin II effect) |
| $10^{-9}M$ | 18.7 ± 2.2 |
| $10^{-8}M$ | 8.1 ± 1.5 |
| $10^{-7}M$ | 5.15 ± 1.6 |
| $10^{-6}M$ | 0.93 ± 0.4 |
| $10^{-5}M$ | 0.9 ± 0.45 |

The contracting effect of angiotensin II on the ciliary artery is quantitatively abolished using valsartan.

EXAMPLE 5

A perfused isolated pig's eye is first treated as described above with a control solution and then with a solution comprising angiotensin II ($10^{-6}M$). After the determination of the angiotensin II effect, valsartan ($10^{-5}M$) is additionally added on top of the above exposure. The relative ophthalmic flow rate resulting in this way is shown below.

| Active ingredient | Decrease in the relative ophthalmic flow (in %) |
|---|---|
| Control | 0.9 ± 2.14 |
| Angiotensin II ($10^{-6}M$), (AII) | 24.5 ± 3.05 |
| AII + valsartan ($10^{-5}M$) | 6.82 ± 3.02 |

The blood flow- decreasing action of angiotensin II is strongly reduced by valsartan.

What is claimed is:

1. A method of treating normal tension glaucoma, which method comprises administering a therapeutically effective amount of an angiotensin II antagonist or of a pharmaceutically acceptable salt thereof to a patient in need of such treatment, wherein said angiotensin II antagonist and salt thereof have pronounced selectivity for the $AT_1$ receptor.

2. The method of claim 1, wherein the angiotensin II antagonist is selected from the group consisting of:

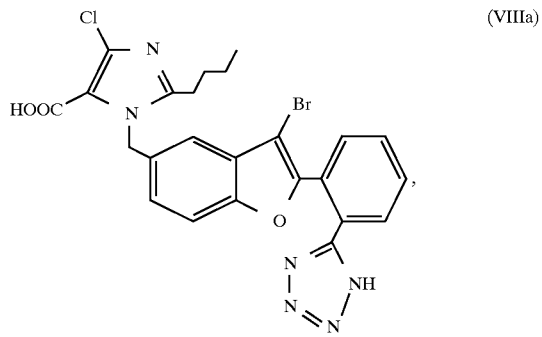

(VIIIa)

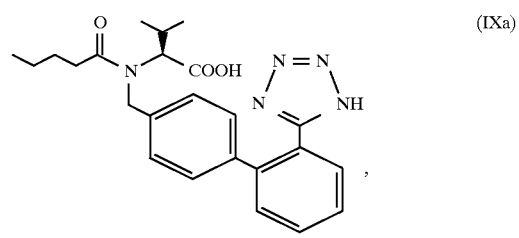

(IXa)

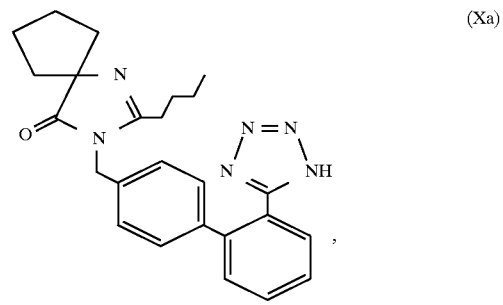

(Xa)

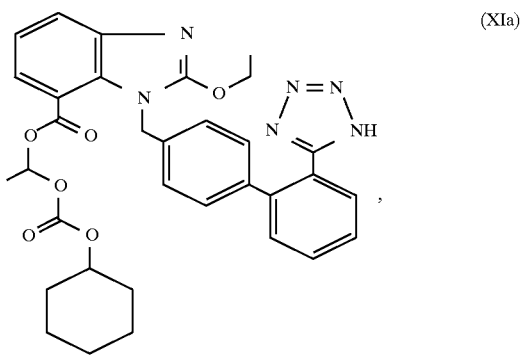

(XIa)

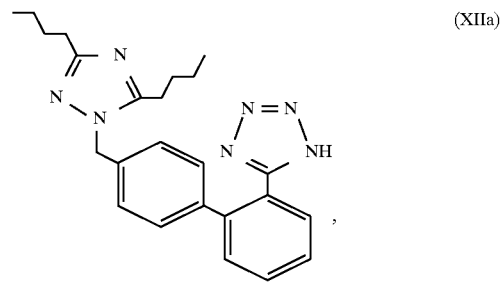

(XIIa)

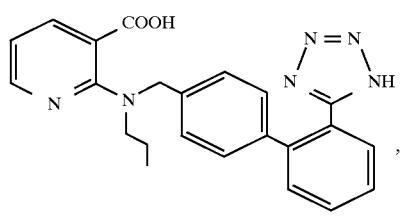 (XIIIa)
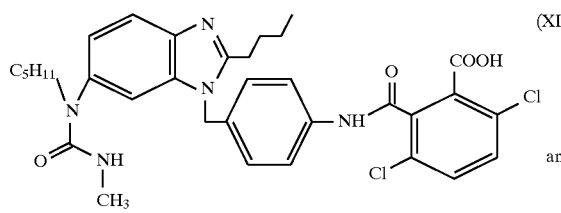 (XIVa) and
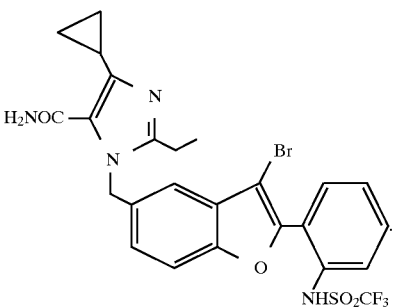 (XVa)
3. The method of claim 2, wherein the angiotensin II antagonist is losartan or valsartan.
4. The method of claim 1, wherein said angiotensin II antagonist and salt thereof have a preference equal to or greater than 99% for the $AT_1$ receptor in comparison to the $AT_2$ receptor.
* * * * *